United States Patent
Boudreau

(10) Patent No.: US 7,579,516 B2
(45) Date of Patent: Aug. 25, 2009

(54) PROMOTERS FUNCTIONAL IN PLANT PLASTIDS

(75) Inventor: Eric Boudreau, Research Triangle Park, NC (US)

(73) Assignee: Syngenta Participations AG (CH)

( * ) Notice: Subject to any disclaimer, the term of this patent is extended or adjusted under 35 U.S.C. 154(b) by 93 days.

(21) Appl. No.: 11/866,500

(22) Filed: Oct. 3, 2007

(65) Prior Publication Data

US 2008/0044905 A1 Feb. 21, 2008

Related U.S. Application Data

(62) Division of application No. 11/262,646, filed on Oct. 31, 2005, now Pat. No. 7,297,839, which is a division of application No. 10/957,562, filed on Oct. 1, 2004, now Pat. No. 7,129,397.

(60) Provisional application No. 60/509,002, filed on Oct. 6, 2003.

(51) Int. Cl.
*C12N 15/82* (2006.01)
*C12N 15/11* (2006.01)

(52) U.S. Cl. .................... 800/278; 435/320.1; 536/24.1

(58) Field of Classification Search ........................ None
See application file for complete search history.

(56) References Cited

U.S. PATENT DOCUMENTS

| | | | |
|---|---|---|---|
| 5,451,513 A | 9/1995 | Maliga | 800/278 |
| 5,545,817 A | 8/1996 | McBride | 800/287 |
| 5,545,818 A | 8/1996 | McBride | 800/279 |
| 5,576,198 A | 11/1996 | McBride | 435/91.3 |
| 5,925,806 A | 7/1999 | McBride | 800/298 |
| 2002/0137214 A1 | 9/2002 | Daniell | 435/468 |
| 2003/0177521 A1 | 9/2003 | Nehra | 800/278 |

FOREIGN PATENT DOCUMENTS

| | | |
|---|---|---|
| WO | WO 95/16783 | 6/1995 |
| WO | WO 97/32011 | 9/1997 |
| WO | WO 97/32977 | 9/1997 |
| WO | WO 03/000727 | 1/2003 |

OTHER PUBLICATIONS

Beck et al (1989, J. Mol. Biol. 210:687-701).*
Bock, R., *Transgenic Plastids in Basic Research and Plant Biotechnology* Journal of Molecular Biology, vol. 312 (2001) pp. 425-438.
Bogorad, L., *Engineering chloroplasts: an alternative site for foreign genes, proteins, reactions and products* Trends in Biotechnology, Vol. 18 (2000) pp, 257-263.
Kuroda and Maliga, *Complementarity of the 16S rRNA penultimate stem with sequences downstream of the AUG destabilizes the plastid mRNAs* Nucleic Acid Research, Vol. 29 (2001) pp. 970-975.
McBride et al., *Controlled expression of plastid transgenes in plants based on a nuclear DNA-encoded and plastid-targeted T7 RNA polymerase* Proceedings of the National Academy of Sciences, USA, vol. 91 (1994) pp. 7301-7305.
Suzuki et al., *Unique Architecture of the Plastid Ribosomal RNA Operon Promoter Recognized by the Multisubunit RNA Polymerase in Tobacco and Other Higher Plants* The Plant Cell, vol. 15 (Jan. 2003) pp. 195-205.
Svab et al., High-frequency plastid transformation in tobacco by selection for a chimeric aadA gene. *Proceedings of the National Academy of Sciences*, USA, vol. 90 (3),(1993) pp. 913-917.
Ye et al. *Plastid-expressed 5-enolpyruvylshikimate-3-phosphate synthase genes provide high level glyphosate tolerance in tobacco* The Plant Journal, vol. 25 (2001) pp. 261-270.

* cited by examiner

*Primary Examiner*—Anne R Kubelik
(74) *Attorney, Agent, or Firm*—Gregory W. Warren

(57) ABSTRACT

The present invention relates to isolated nucleic acid molecule comprising the untranslated region of SEQ ID NO: 1, 2 or 3. The invention also relates to chimeric genes comprising SEQ ID NO: 2 operatively linked to the coding sequence of a gene of interest and to plant transformation vectors comprising the chimeric genes of the invention. The invention further relates to transgenic plants, plant cells, plant seeds, plant tissues, or plant plastids comprising the chimeric gene.

5 Claims, 1 Drawing Sheet

PROMOTERS FUNCTIONAL IN PLANT PLASTIDS

This application is a divisional of U.S. patent application Ser. No. 11/262,646 filed Oct. 31, 2005 now U.S. Pat. No. 7,297,839, which is a divisional of U.S. patent application Ser. No. 10/957,562, filed on Oct. 1, 2004 now U.S. Pat. No. 7,129,397, which claims the benefit of U.S. Provisional Patent Application No. 60/509,002, filed on Oct. 6, 2003, which are incorporated herein by reference in their entireties.

FIELD OF THE INVENTION

This invention is in the field of gene promoter nucleic acid sequences and their use in expression of nucleic acid sequences in plant plastids. The following invention provides nucleic acid sequences of non-plastid origin useful for the expression of transgenic genes in plastids. The invention also relates to methods of using the novel promoters in plant plastids. The invention further relates to recombinant nucleic acid molecules comprising nucleic acid molecules encoding the novel promoters. Also, the invention relates to plastids, host cells, plants or progeny thereof comprising the nucleic acid molecules or recombinant molecules described herein.

BACKGROUND OF THE INVENTION

There are only a limited number of genie regulatory elements such as promoters, 5'untranslated region (5'UTR) and 3'untranslated region (3'UTR) available for plastid transgene expression and most of them are plastid sequences. As plastid genomes are highly active in homologous recombination, the insertion in the genome of endogeneous sequences as regulatory element could bring about genomic rearrangements resulting in loss or inactivation of the transgenic function. In order to prevent such genomic rearrangement, foreign sequences sharing little homology with plastid genomic DNA sequence should be used as regulatory elements for plastid transgene expression.

In land plant plastids, the mRNA 5'UTR sequences are essential for mRNA stability and translation initiation process. The 5'UTRs of most highly expressed plastid genes contain a Shine-Dalgarno like sequence that is complimentary to the 3' end of the plastid 16S rRNA. and is believed to play a predominant role in translation initiation. It is possible that foreign sequences that contain a Shine-Dalgarno like sequence might be able to function as plastid gene translation element. The bacteriophage T7 gene 10 5'UTR sequence, which contains a SD element, was previously shown to be very efficient in promoting translation in plastids (McBride et al., (1994) Proc. Natl. Acad. Sci. 91: 7301-7305; Ye et al., (2001) Plant J. 25: 261-270; Kuroda and Maliga (2001) Nucl. Acids Res. 29: 970-975).

SUMMARY OF THE INVENTION

The present invention relates to isolated nucleic acid molecule comprising a nucleic acid promoter or untranslated region comprising the nucleic acid sequence of SEQ ID NO: 1, 2 or 3 wherein the promoter or untranslated region is functional as a promoter in a plant plastid. The invention also relates to isolated nucleic acid promoter or untranslated region comprising the nucleic acid sequence of SEQ ID NO: 1, 2 or 3. The invention further relates to chimeric genes comprising the isolated nucleic acid promoter of SEQ ID NO:1, 2 or 3 operatively linked to the coding sequence of a gene of interest. The invention also relates to plant transformation vectors comprising the chimeric genes of the invention. The invention further relates to transgenic plants, plant cells, plant seeds, plant tissues, or plant plastids, comprising the chimeric genes of this invention.

BRIEF DESCRIPTION OF THE SEQUENCES IN THE SEQUENCE LISTING

SEQ ID NO:1 is the nucleic acid sequence of the *Staphyloccus aureus* bacteriophage X2 promoter.

SEQ ID NO:2 is the nucleic acid sequence of the *Kluyvera* bacteriophage kvpI gene 10 5' untranslated region (UTR).

SEQ ID NO:3 is the nucleic acid sequence of the Bacteriophage T3 gene 9 5' UTR.

SEQ ID NO:4 is the nucleic acid sequence of the plasmid pEB10 plastid transformation vector.

SEQ ID NO:5 is the nucleic acid sequence of the top strand primer comprising an introduced XbaI restriction site at the 5'end of the kvpI gene 10 5'UTR region.

SEQ ID NO:6 is the nucleic acid sequence of the bottom strand primer of the kvpI gene 10 5'UTR comprising an introduced NcoI restriction site overlapping the ATC initiation codon.

SEQ ID NO:7 is the nucleic acid sequence of the top strand primer for the maize 16S NEP-PEP promoter gene comprising an introduced EcoRI restriction at the 5' end of the 16S rRNA gene promoter region.

SEQ ID NO:8 is the nucleic acid sequence of the bottom strand primer for the maize 16S NEP-PEP promoter gene comprising an introduced XbaI restriction site at the 3' end of the 16S rRNA gene promoter region.

SEQ ID NO:9 is the nucleic acid sequence of the top strand primer (RTK36) comprising an introduced NcoI restriction site at the 3' end of the T3 gene 9 5'UTR.

SEQ ID NO:10 is the nucleic acid sequence of the bottom strand primer (RTK39) comprising an introduced SmaI site at the 5' end of the 5'UTR.

SEQ ID NO:11 is the nucleic acid sequence of the top strand primer (RTK38) comprising an introduced SmaI restriction site at the 3' end of the Maize 16S PEP-NEP promoter.

SEQ ID NO:12 is the nucleic acid sequence of bottom strand primer (RTK37) comprising an introduced BspHI site at the 3' end of the psbA 5'UTR.

SEQ ID NO:13 is the nucleic acid sequence of the top strand of oligonucleotide of the bacteriophage X2 promoter-like sequence.

SEQ ID NO:14 is the nucleic acid sequence of the bottom strand oligonucleotide of the bacteriophage X2 promoter-like sequence.

SEQ ID NO:15 is the nucleic acid sequence of the chimeric *Staphylcoccus aureaus* bacteriophage X2 promoter like-sequence fused to the bacteriophage kvpI gene 10 5'UTR.

DEFINITIONS

Figure 1:
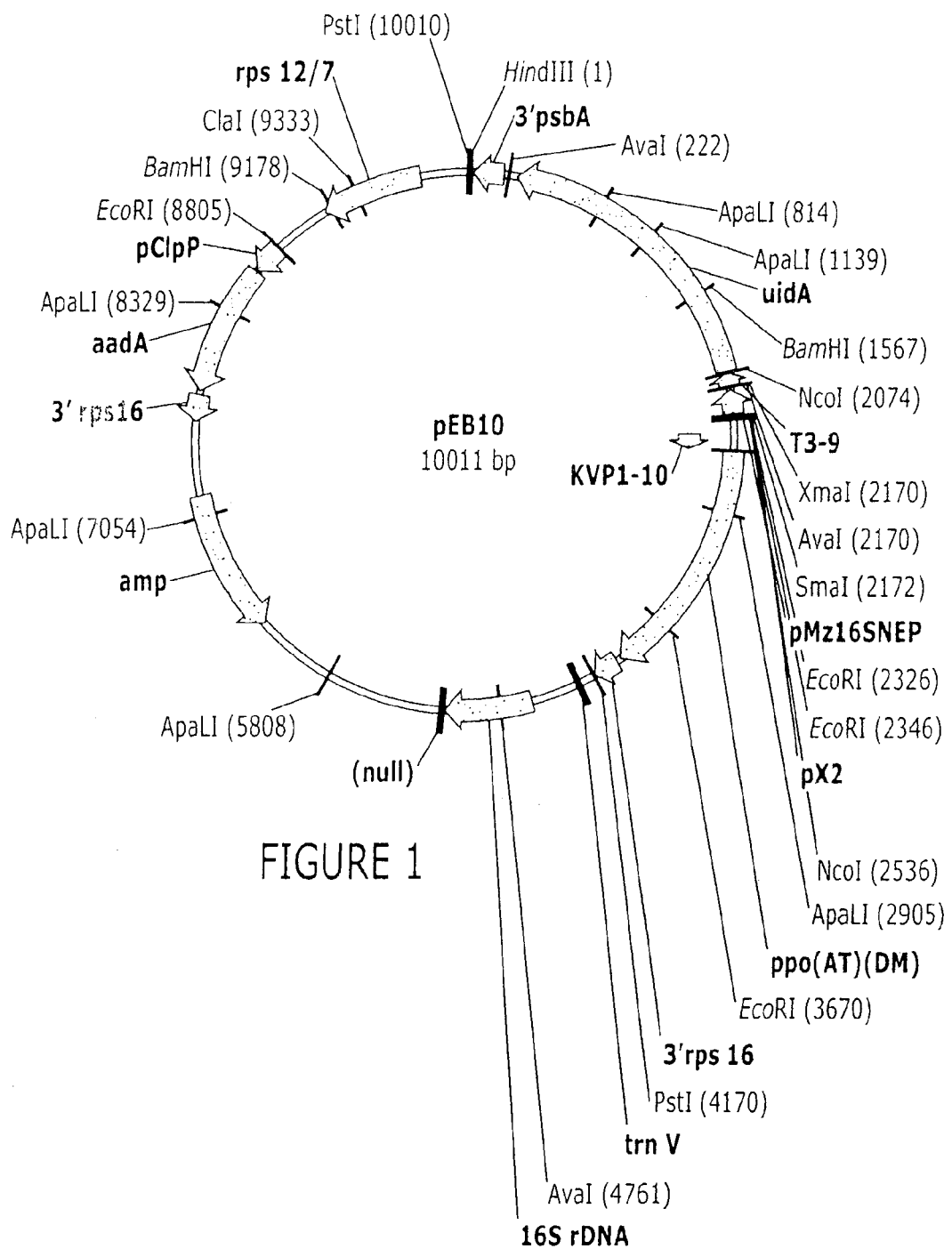
FIG. 1 shows the restriction enzyme map of plasmid pEB10.

For clarity: certain terms used in the specification are defined and presented as follows:

Associated With/Operatively Linked: refers to two nucleic acid sequences that are related physically or functionally. For example, a promoter of regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene/Fusion Sequence: a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

Coding Sequence: nucleic acid sequence that is transcribed into RNA such as mRNA, rRNA, tRNA, snRNA, sense RNA or antisense RNA. Preferably the RNA is then translated in an organism to produce a protein.

Gene: a defined region that is located within a genome and that, besides the aforementioned coding sequence, comprises other, primary regulatory, sequences responsible for the control of the expression, that is to say the transcription and translation, of the coding portion. A gene may also comprise other 5' and 3' untranslated sequences and termination sequences. Further elements that may, be present are, for example introns.

Gene of Interest: any gene that, when transferred to a plant, confers upon the plant a desired characteristic such antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

Heterologous Nucleic Acid Sequence: a nucleic acid sequence not naturally associated with the host genome into which it is introduced, including non-naturally occurring multiple copies of a naturally occurring nucleic acid sequence.

Homologous Nucleic Acid Sequence: a nucleic acid sequence naturally associated with a host genome into which it is introduced.

Homologous Recombination: the reciprocal exchange of nucleic acid fragments between homologous nucleic acid molecules.

Isolated: in the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a transgenic host cell.

Minimal Promoter: promoter elements that are inactive or that have greatly reduced promoter activity in the absence of upstream activation. In the presence of a suitable transcription factor, the minimal promoter functions to permit transcription.

Nucleic Acid Molecule 1 Nucleic Acid Sequence: a linear segment of single- or double-stranded DNA or RNA that can be isolated from any source. In the context of the present invention, the nucleic acid molecule is preferably a segment of DNA.

Plant: any plant at any stage of development, particularly a seed plant.

Plant Cell: a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

Plant Cell Culture: cultures of plant units such as, for example, protoplasts, cell culture cells, cells in plant tissues, pollen, pollen tubes, ovules, embryo sacs, zygotes and embryos at various stages of development.

Plant material: leaves, stems, roots, flowers or flower parts, fruits, pollen, egg cells, zygotes, seeds, cuttings, cell or tissue cultures, or any other part or product of a plant.

Plant Organ: a distinct and visibly structured and differentiated part of a plant such as a root, stem, leaf, flower bud, or embryo.

Plant tissue: as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Promoter: an untranslated DNA sequence upstream of the coding region that contains the binding site for RNA polymerase 11 and initiates transcription of the DNA. The promoter region may also include other elements that act as regulators of gene expression.

Protoplast: an isolated plant cell without a cell wall or with only parts of the cell wall.

Regulatory Sequence: an untranslated nucleic acid sequence that assists in, enhances, or otherwise affects the transcription, translation or expression of an associated structural nucleic acid sequence that codes for a protein or other gene product. Regulatory sequences include promoters. A promoter sequence is usually located at the 5' end of a translated sequence, typically between 20 and 100 nucleotides from the 5' end of the translation start site. Regulatory sequences may also include transcribed but untranslated nucleic acid sequences located 5' and 3' to coding sequences. These untranslated RNA's are typically involved in post-transcriptional regulation of gene expression.

Substantially Similar: with respect to nucleic acids, a nucleic acid molecule that has at least 60 percent sequence identity with a reference nucleic acid molecule. In a preferred embodiment, a substantially similar DNA sequence is at least 80% identical to a reference DNA sequence; In a more preferred embodiment a substantially similar DNA sequence is at least 90% identical to a reference DNA sequence; and in a most preferred embodiment, a substantially similar DNA sequence is at least 95% identical to a reference DNA sequence. A substantially similar nucleotide sequence typically hybridizes to a reference nucleic acid molecule, or fragments thereof, under the following conditions, hybridization at 7% sodium dodecyl sulfate (SDS), 0.5 M NaPO.sub.4 pH 7.0, 1 mM EDTA at 50.degree. C.; wash with 2.times.SSC, 1% SDS, at 50.degree. C. With respect to proteins or peptides, a substantially similar amino acid, sequence is an amino acid sequence that is at least 90% identical to the amino acid sequence of a reference protein or peptide and has substantially the same activity as the reference protein or peptide.

Tolerance: the ability to continue normal growth or function when exposed to an inhibitor or herbicide.

Transformation: a process for introducing heterologous DNA into a cell, tissue, or plant, including a plant plastid. Transformed cells, tissues, or plants are understood to encompass not only the end product of a transformation process, but also transgenic progeny thereof;

Transformed/Transgenic/Recombinant: refer to a host organism such as a bacterium or a plant into which a heterologous nucleic acid molecule has been introduced. The nucleic acid molecule can be stably integrated in to the genome of the host or the nucleic acid molecule can also be present as an extra chromosomal molecule. Such an extrachromosomal molecule can be auto-replicating. Transformed cells, tissues, or plants are understood to encompass not only the end product of a transformation process, but also transgenic progeny thereto. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DETAILED DESCRIPTION OF THE INVENTION

The present invention provides the X2 promoter from the bacteriophage *Staphylococcus aureus* having the nucleotide sequence of SEQ ID NO:1, the *Kluyvera* bacteriophage kvpI gene 10 5' untranslated region (UTR) having the nucleotide sequence of SEQ ID NO2, and the Bacteriophage T3 gene 9 5'UTR having the nucleotide sequence of SEQ ID NO:3 which function as promoters in plant plastids. The disclosed promoter and untranslated regions can be used to drive expression of coding sequences for selectable marker genes or any other genes of interest in the plastids of transgenic plants. The promoter and untranslated region is of the present invention is useful for constitutive expression of transgenes in both green and non-green plastids and is therefore particularly useful for plastid transformation in plants such as maize, in which selection of regenerable transformants requires selection in non-green tissues.

The promoter and untranslated regions of the present invention can be incorporated into plastid transformation vectors and transformed into plastids according to methods known in the art, particularly those described in the following: U.S. Pat. Nos. 5,451,513, 5,545,817, 5,545,818, and 5,576,198; Intl. Application Nos. WO 95/16783, WO 97/32011, and WO 97/32977, and Svab et al. (1993) and Mcbride et al. (1994), Plastid gene transformation is an important alternative for the expression of heterologous genes in plants (reviewed by Bogorad, Trends Biotechnol. 18: 257-263, 2000 and Bock, J. Mol. Biol. 312: 425-438, 2001). Although plastid genomes are relatively small in size, 120 to 160 kb, they can easily accommodate several kilo bases of foreign DNA within them. Insertion of foreign DNA in the plastid genome mainly occurs via homologous recombination and a transgene can be site directed at a particular locus using suitable homologous flanking regions. One of the major, advantages of plastid transformation is that it is possible to obtain very high transgene expression. The plastid genome (plastome) is highly polyploid so the transgene is expressed from multiple gene copies in the plastid. The polyploidy of the plastid genome is such that a mature leaf cell may contain over 10,000 copies of the plastome. Also contributing to the high level of the plastid transgene expression is absence of position effect and gene silencing. Another major advantage is that plastids from most crop plants are only maternally inherited and thus, the ecological risk of plastid transgene escape through pollen-mediated out crossing is minimized.

The basic DNA delivery techniques for plastid transformation are either via particle bombardment of leaves or polyethylene glycol mediated DNA uptake in protoplasts. Plastid transformation via biolistics was initially achieved in the unicellular green alga *Chlamydomonas reinhardtii* (Boynton et al., Science 240: 1534-1537, 1988) and this approach, using selection for cis-acting antibiotic resistance loci (spectinomycin streptomycin resistance) or complementation of non-photosynthetic mutant phenotypes, was extended to *Nicotiana tabacum* Svab et al., Proc. Natl. Acad. Sci. USA 87-8526-8530), 1990), *Arabudiosus* (Sikdar et al., Plant Cell Reports 18:20-24, 1991), *Brassica napus* (WO 00/39313), potato (Sidorov et al., The Plant Journal 19(2): 209-216, 1999), petunia (W)O 00/28014), tomato (Ruf et al., Nature Biotechnology 19: 870-875, 2001), oilseed rape (Hou et al., Transgenic Res. 12: 111-114, 2003) and *Lesquerella Fendleri* (Skarjinskaia et al., transgenc Res. 12: 115-122 ,2003). Plastid tranforvation of protoplasts from tobacco and the moss *Physcomitrella patens* has been attained using polyethylene glycol (PEG) mediated DNA uptake (O'Neill et al., Plant J. 3: 729-738, 1993; Koop et al., Plant 199: 193-201, 1996). More recently, micro-injection of DNA directly in plastids of marginal mesophyll cells of intact tobacco plant resulted in transient expression (Knoblauch et al., Nature Biotechnology 17: 906-909, 1999) but stable transformants using this technique have yet to be reported. Stable chloroplast transformation by biolistics was also reported for the Euglenophyte *Eugena gracilis* (Doetsch et. al., Curr Genet. 39:49-60, 2001) and the unicellular red alga *Porphyridium* sp. (Lapidot et al., Plant Physiol. 129: 7-12, 2002), the dominant selectable marker used for latter consist of a mutant form of the gene encoding acetohydroxyacid synthase which confers tolerance to the herbicide sulfometuron methyl. As previously mentioned, chloroplast transformation consists of integrating a foreign DNA at a precise position in the plastid genome by homologous recombination. The plastid transformation vectors consist of cloned plastid DNA, homologous to the targeted region, which flanks a selectable marker gene which itself is linked to a gene or several genes of interest. After transformation, the transgene(s) and the selectable marker are inserted together as a block of heterologous sequence in the targeted locus of the plastid genome via homologous recombination between the vectors plastid sequence and the targeted locus. In order to obtain stably transformed homoplasmic plants, i.e. plants having the foreign DNA inserted into every plastome copy of the plant cell, several rounds of subculture on selective media are required. This process facilitates the segregation of transplastomic and untransformed plastids and results in the selection of homoplasmic cells with gene(s) of interest and the selectable marker stably integrated into the plastome, since these genes are linked together.

Most stable plastid transformation demonstrated to date has been based on selection using the antibiotic resistance gene aadA (as referenced above) or NPTII (Carter et al., Mol Gen Genet 241:49-56, 1993), to obtain homoplasmic plants. These selectable markers confer a specific selection phenotype, the green pigmentation (U.S. Pat. No. 5,451,513), which allows to visually distinguish the green pigmented transplastomic cells from cells having wild-type plastids which are non pigmented under selection conditions.

most plastid transformation methods rely on the use of a selectable marker that confers a non-lethal selection. These selectable markers also confer a specific selection phenotype, the green pigmentation (U.S. Pat. No. 5,451,513) which allows one to visually distinguish the green pigmented transplastomic cells from cells having wild-type plastids that are non-pigmented under selection conditions. For example, plants transformed with the bacterial aadA gene which conifers resistance to spectinomycin and streptomycin grow normally in the presence of either one of these antibiotics whereas untransformed plants are bleached. Transformed plants can thus easily be identified using chlorophyll as a visual marker. There is a limited number of selectable markers available for plastid transformation and the most reliable ones, such as aaadA or point mutations in the plastid 16S rDNA and rps12 genes, confer resistance to the same antibiotics, spectinomycin and/or streptomycin. Selectable markers conferring resistance to other antibiotics such as kanamycin were shown to be much less effective for plastid transformation.

The present invention further provides a method of using novel plastid promoters, such as the X2 promoter of SEQ ID NO:1, the *Kluyvera* bacteriophage kvpI gene 10 5' untranslated region (UTR) having the nucleotide sequence of SEQ ID NO;2, and the Bacteriophage T3 gene 9 5' UTR to improve plastid transformation efficiency by reducing undesired recombination between native DNA sequences in the plastid genome and exogenous DNA sequences contained in chimeric DNA fragments that are incorporated into plastid transformation vectors. It is known that even relatively short regions of homology between native DNA sequences in the plastid genome and exogenous DNA sequences will ultimately cause somatic recombination in plastid transformants. This biological property has even been used as a means for eliminating selectable markers from plastid transformants in chloroplasts of the green alga (Chlamydomonas by flanking the selectable marker with identical repeated heterologous DNA sequences. Although neither the minimum size tract of homology required nor the precise degree of sequence identity within a particular homology tract sufficient for recombination has been identified, as little as 50-bp of homology to the plastid genome may be enough to induce recombination. These recombination events are visible in transgenic plants as pale sectors in leaves resulting from division of cells in which plastid genome rearrangements have occurred. In extreme cases the result is nearly white leaves with small patches of green indicating recombination occurring in the majority of somatic cells and their lineage.

The essential features of non-recombinogenic regulatory sequences (such as promoters and 5' and 3' UTR's) include both the ability to function correctly to control heterologous gene expression in the plastids of a plant species of interest, as well as the lack of sufficient sequence identity to promote homologous plastid recombination. The latter property may be achieved either by using a heterologous regulatory sequence derived from the plastid genome of a different plant species, which has diverged in sequence to less than 8590% identity, or by sufficiently mutating a native regulatory sequence derived from the plastid genome of the same plant species. In one embodiment this method involves using the X2 promoter or 5'UTRs of the present invention to direct transcription of genes of interest in the plastids of heterologous plant species such as tobacco, maize, rice, soybean, tomato, potato, or others. In another embodiment this method involves using the X2 promoter or 5'UTRs described in the Examples to direct transcription of genes of interest in the plastids of heterologous plant species such as tobacco, maize, rice, soybean, tomato, potato, or others.

The invention will be further described by reference to the following detailed examples. These examples are provided for purposes of illustration only, and are not intended to be limiting unless otherwise specified.

EXAMPLES

Example 1

Making of Plastid Transformation Vector having PPO has Selectable Marker which is Under the Control of the Bacteriophage X2 Promoter Amplification of the bacteriophage kvpI gene 10 5'UTR The kvpI gene 10 5'UTR was isolated by PCR amplification from a plasmid containing kvpI gene 10 using a top strand primer comprising an introduced XbaI restriction site at the 5'end of the 5'UTR region (5'GT TCTAGAGACATTACGTTCTCCCCTTG3' (SEQ ID NO:5) (XbaI site is underlined) and a bottom strand primer comprising an introduced NcoI restriction site overlapping the ATG initiation codon (5'AGATAT CCATGGTGAATCTCCTGTTGATT3' (SEQ ID NO:6) (NcoI restriction site is underlined)). PCR amplification of a 119 bp fragment was performed with taq DNA Polymerase kit (QIAGEN, Valencia Calif.) in a Perkin Elmer Thermal Cycler 480according to the manufacturer's recommendations (Perkin Elmer/Roche, Branchburg, N.J.) as follows 5 min 95° C., followed by 5 cycles of 1 min 95° C./15 sec 72° C., then 25 cycles of 1 min 95° C./1 min 55° C./15 sec 72° C.

Plasmid pEBPKVP-10 was created by ligating together the 105 bp XbaI-NcoI fragment from the kvpI gene 10 5'UTR amplified fragment within an 8.0 kb XbaI-NcoI fragment from pEBPaccD vector. Plasmid pEBPKVP10-GFP was created by ligating a 5.2 kb NcoI-BamHI fragment from pEBP-KVP10 with a 1.8 Kb fragment from pPB69b, containing GFP gene linked to *A. thaliana* plastid psbA 3'UTR.

The maize 16S NEP-PEP promoter was amplified by PCR from pPB98 using a top strand primer comprising an introduced EcoRI restriction at the 5'end of the 16S rRNA gene promoter region (5'GCCA GAATTCACCACGATCGAACGGGAATGGATA3' (SEQ ID NO:7) (EcoRI site is underlined)) and a bottom strand primer comprising an introduced XbaI restriction site at the 3' end of the 16S rRNA gene promoter region (5' GC TCTAGAGATTCGGAATTGTCTTTCCTT 3' (SEQ ID NO:8) (XbaI restriction site is underline)). PCR amplification of a 164 bp fragment was performed with the Pfu Turbo DNA polymerase kit (Stratagene, LaJolla, Calif.) in a Perkin Elmer Thermal Cycler 480 according to the manufacturer's recommendations (Perkin Elmer/Roche, Branchburg, N.J.) as follows 5 min 95° C., followed by 35 cycles of 1 min 95° C./1 min 50° C./15 sec 72° C.

The amplified 16rRNA promoter sequence was cut with XbatI and EcoRI and the resulting 152 bp fragment was ligated to a 6.0 kb XbaI-EcoRI fragment from pB98 plasmid transformation vector. The resulting plasmid was subsequently cut with XbaI and BamHI and a 5.1 kb fragment isolated from the digest was ligated with a 1.9 kb xbaI- BaMHI fragment from pEBPKVP10-GFP, containing the kvpI gene 10 5'UTR::GFP::*A.thaliana* psbA 3'UTR chimeric, to give pEBM16SKGFP.

Example 2

Construction of Plasmid RTK7

The 116 bp bacteriophage T3 gene 5'UTR was PCR amplified from a plasmid using a top strand primer (RTK-36) comprising an introduced NcoI restriction site at the 3'end of the T3 gene 9 5'UTR (5'GAAGATG CCATGGATTAAATCTCCTAAGTTATTAAAG 3' (SEQ ID NO:9) (NcoI site is underlined)) and a bottom strand primer (RTK39) comprising an introduced SmaI site at the 5' end of the 5' end of the 5'CGAATCTCTT CCCGGGTAGAGGGAGACCTCATCTTTG 3' (SEQ ID NO:10) (SmaI restriction site is underlined)). A 328 bp fragment having the Maize 16S PEP-NEP rRNA gene promoter and tobacco psbA gene promoter was PCR amplified from pEBT3-9 GFP using a top strand primer (RTK38) comprising an introduced SmaI restriction site at the 3'end of the Maize 16S PEP-NEP promoter (5' CTCCCTCTA CCCGGGAAGAGATTCGGAATTGTCTTTCC 3' (SEQ ID NO:11) (SmaI site is underlined)) and a bottom strand primer (RTK37) comprising an introduced BspHI site at the 3' end of the psbA 5'UTR (5' CGCTTAG TCATGATAAAATCTTGGTTTATTTAATCATC 3' (SEQ ID NO:12) (BspHI restriction site is underlined)). PCR products were purified, mixed together at equal molar ratio with primers RTK36 and RTK37 and mixture was used to PCR amplify, a 421bp fragment. PCRs were performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg, N.J.).

To make plasmid RTK7, the plasmid RTK6 having the protoporphyrinogen oxidase (ppo) and β-glucuronidase (gus) genes cloned in opposite orientation was first created by ligating a 7.5 kb HindIII-NcoI fragment from pEB8a, the transformation vector with ppo::*N. tabacum* rps 3'UTR chimeric gene with a 2.1 kb HindIII-NcoI fragment containing gus::*A.thaliana* psbA 3'UTR gene from plasmid pEBPkvp10. Plasmid RTK7 was eventually made by ligating a NcoI linearized 9.6 kb RTK6 with the 405 bp NcoI-BspHI PCR amplified Maize 16S and psbA promoters. Only the plasmid having psbA promoter driving ppo and Maize 16S PEP-NEP promoter driving gus was retained.

Example 3

Construction of a Bacteriophage X2 Promoter-like Sequence Fused to the kvpI Gene 10 5'UTR: GFP::*A. thaliana* Plasmid psbA 3'UTR Chimeric Gene An 85 bp EcoRI-XbaI fragment consisting of the bacteriophage X2 promoter-like sequence was created by annealing together a top stand oligonucleotide (5'AATTCGT-TAAAGAATGTAGCTGACTGCATACTTAAACCACCCA TACTAGTTGCTG GGTGGTTTTTATGT-TATAATATAAATGTGT 3') (SEQ ID NO:13) with the following complimentary bottom strand oligonucleotide (5'CTAGACACATTTATATTATAACAT-AAAAACCACCCAGCAACTAGTATGGGTGGTT TAAG-TATGCAGTCAGCTACATTCTTTAACG 3') (SEQ ID NO:14) Plasmid PEBX2 was created by ligating the created 85 bp EcoRI-XbaI fragment with a 6.8 kb ECoRI-XbaI fragment from pEBZM16SKGFP plasmid, containing the kvpI gene 10 5'UTR::GFP ::*A. thaliana* psbA 3'UTR with the remainder of the plastid transformation vector. The nucleotide sequence of the chimeric *Staphylococcus aureaus* bacteriophage X2 promoter like-sequence fused to the bacteriophage kvpI gene 10 5'UTR is in SEQ ID NO:15.

Example 4

Construction of Plastid Transformation Vector pEB10

Plasmid pEB9 was created by ligating a 200 bp BglII-NcoI fragment from pEBX-2, containing the X2 promoter like sequence fused to the kvpI gene 10 5'UTR, and a 8.5 kb BglII-NcoI from pEB8a (described in case 70149) plastid transformation vector. The final pEBL10 plasmid transformation vector (see FIG. 1) was created by ligating a 7.8 kb BglII-HindIII fragment from pEB9 with a 2.3 kb fragment from pRTK7, containing the chimeric gene pMz16SNEP:: T3-9 5'UTR:: uidA:: 3'psbA.

Example 5

Plasmid Transformation with pEB10

Resulting chimeric reporter gene was stably introduced in tobacco plastid genome using plastid transformation dual selection protocol described in International Patent Publication No. WO04/035734. Out of 6 plates bombed, one event was found to be able to grow on 50 nM of butafenacyl after two rounds of selection on spectinomycin. After 3 rounds of selection on butafenacyl the event was confirmed by Southern analysis to be homoplasmic for insertion in the chloroplast genomes of the PPO and gus genes. Activity of GUS was visualized by standard GUS assays.

The above-disclosed embodiments are illustrative. This disclosure of the invention place one skilled in the art in possession of many variations of the invention. All such obvious and foreseeable variations are intended to be encompassed by the present invention.

Numerous patents, applications and references are discussed or cited within this specification, and all are incorporated by reference in their entireties.

What is claimed is:

1. An isolated nucleic acid molecule comprising an untranslated region comprising the nucleic acid sequence of SEQ ID NO: 3 wherein thee untranslated region is functional as a promoter in a plant plastid.

2. An isolated nucleic acid untranslated region comprising the nucleic acid sequence of SEQ ID NO: 3.

3. A chimeric gene comprising the nucleic acid molecule of claim 1 operatively linked to the coding sequence of a gene of interest.

4. A plant transformation vector comprising the chimeric gene of claim 3.

5. A transgenic plant, plant cell, plant seed, plant tissue, or plant plastid, comprising the chimeric gene of claim 3.

* * * * *

UNITED STATES PATENT AND TRADEMARK OFFICE
CERTIFICATE OF CORRECTION

PATENT NO. : 7,579,516 B2
APPLICATION NO. : 11/866500
DATED : August 25, 2009
INVENTOR(S) : Eric Boudreau It is certified that error appears in the above-identified patent and that said Letters Patent is hereby corrected as shown below:

Col. 25, Claim 1, line 13, please replace "thee" with --the--.

Signed and Sealed this

Seventeenth Day of November, 2009

David J. Kappos
*Director of the United States Patent and Trademark Office*

SEQUENCE LISTING

<160> NUMBER OF SEQ ID NOS: 15

<210> SEQ ID NO 1

```
<211> LENGTH: 79
<212> TYPE: DNA
<213> ORGANISM: Staphylococcus aureus

<400> SEQUENCE: 1
gttaaagaat gtagctgact gcatacttaa accacccata ctagttgctg ggtggttttt      60
atgttataat ataaatgtg                                                   79

<210> SEQ ID NO 2
<211> LENGTH: 110
<212> TYPE: DNA
<213> ORGANISM: Kluyvera

<400> SEQUENCE: 2
tctagagaca ttacgttctc cccttgagtg atacacaatg agaaccaact cgtttcaagt      60
agtacctcac ataacttatc ttttaaatca acagaaggag attcaccatg              110

<210> SEQ ID NO 3
<211> LENGTH: 97
<212> TYPE: DNA
<213> ORGANISM: Bacteriophage T3

<400> SEQUENCE: 3
tctagaggga gacctcatct ttgaaatgag cgatgactaa aggttggagt cctttggttt      60
ccctttatct ttaataactt aggagattta attcatg                               97

<210> SEQ ID NO 4
<211> LENGTH: 10011
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (1)..(10011)

<400> SEQUENCE: 4
agcttctaat aaaaaatata tagtaatttt ttattattta ttattattat ttattattaa      60
tataataaat aaagtaaaat atgatactct ataaaaattt gctcattttt atagaaaaaa    120
acgagtaata taagccctct ttcttattta agaaggctt atattgctcg ttttttacta     180
aactagattt agactaacac taactagttc tagagcaatt cccgaggctg tagccgacga    240
tggtgcgcca ggagagttgt tgattcattg tttgcctccc tgctgcggtt tttcaccgaa    300
gttcatgcca gtccagcgtt tttgcagcag aaaagccgcc gacttcggtt tgcggtcgcg    360
agtgaagatc cctttcttgt taccgccaac gcgcaatatg ccttgcgagg tcgcaaaatc    420
ggcgaaattc catacctgtt caccgacgac ggcgctgacg cgatcaaaga cgcggtgata    480
catatccagc catgcacact gatactcttc actccacatg tcggtgtaca ttgagtgcag    540
cccggctaac gtatccacgc cgtattcggt gatgataatc ggctgatgca gtttctcctg    600
ccaggccaga agttcttttt ccagtaccct tctctgccgt tccaaatcgc cgcttttggac   660 ataccatccg taataacggt tcaggcacag cacatcaaag agatcgctga tggtatcggt    720
gtgagcgtcg cagaacatta cattgacgca ggtgatcgga cgcgtcgggt cgagtttacg    780
cgttgcttcc gccagtggcg cgaaatattc ccgtgcacct tgcggacggg tatccggttc    840
gttggcaata ctccacatca ccacgcttgg gtggtttttg tcacgcgcta tcagctcttt    900
aatcgcctgt aagtgcgctt gctgagtttc cccgttgact gcctcttcgc tgtacagttc    960
```

-continued

```
tttcggcttg ttgcccgctt cgaaaccaat gcctaaagag aggttaaagc cgacagcagc   1020
agtttcatca atcaccacga tgccatgttc atctgcccag tcgagcatct cttcagcgta   1080
agggtaatgc gaggtacggt aggagttggc cccaatccag tccattaatg cgtggtcgtg   1140
caccatcagc acgttatcga atcctttgcc acgcaagtcc gcatcttcat gacgaccaaa   1200
gccagtaaag tagaacggtt tgtggttaat caggaactgt tcgcccttca ctgccactga   1260
ccggatgccg acgcgaagcg ggtagatatc acactctgtc tggcttttgg ctgtgacgca   1320
cagttcatag agataacctt cacccggttg ccagaggtgc ggattcacca cttgcaaagt   1380
cccgctagtg ccttgtccag ttgcaaccac ctgttgatcc gcatcacgca gttcaacgct   1440
gacatcacca ttggccacca cctgccagtc aacagacgcg tggttacagt cttgcgcgac   1500
atgcgtcacc acggtgatat cgtccaccca ggtgttcggc gtggtgtaga gcattacgct   1560
gcgatggatc ccggcatagt taaagaaatc atggaagtaa gactgctttt tcttgccgtt   1620
ttcgtcggta atcaccattc ccggcgggat agtctgccag ttcagttcgt tgttcacaca   1680
aacggtgata cgtacacttt tcccggcaat aacatacggc gtgacatcgg cttcaaatgg   1740
cgtatagccg ccctgatgct ccatcacttc ctgattattg acccacactt tgccgtaatg   1800
agtgaccgca tcgaaacgca gcacgatacg ctggcctgcc caacctttcg gtataaagac   1860
ttcgcgctga taccagacgt tgcccgcata attacgaata tctgcatcgg cgaactgatc   1920
gttaaaactg cctggcacag caattgcccg gctttcttgt aacgcgcttt cccaccaacg   1980
ctgatcaatt ccacagtttt cgcgatccag actgaatgcc cacaggccgt cgagtttttt   2040
gatttcacgg gttggggttt ctacaggacg gaccatggat aaatctcct aagttattaa    2100 agataaaggg aaaccaaagg actccaacct ttagtcatcg ctcatttcaa agatgaggtc   2160
tccctctacc cgggaagaga ttcggaattg tctttccttc caaggataac ttgtatccag   2220
gcgcttcaga ttattagcct ggagttcgcc accagcagta tagccaaccc taccctatca   2280
cgtcaatccc acaagcctct tatccattcc cgttcgatcg tggtgaattc gaatagatct   2340
attcgaattc gttaaagaat gtagctgact gcatacttaa accacccata ctagttgctg   2400
ggtggttttt atgttataat ataaatgtgt ctagagacat tacgttctcc ccttgagtga   2460
tacacaatga gaaccaactc gtttcaagta gtacctcaca taacttatct tttaaatcaa   2520
cagaaggaga ttcaccatgg attgtgtgat tgtcggcgga ggtattagtg gtctttgcat   2580
cgctcaggcg cttgctacta agcatcctga tgctgctccg aatttaattg tgaccgaggc   2640
taaggatcgt gttggaggca acattatcac tcgtgaagag aatggttttc tctgggaaga   2700
aggtcccaat agttttcaac cgtctgatcc tatgctcact atggtggtag atagtggttt   2760
gaaggatgat ttggtgttgg gagatcctac tgcgccaagg tttgtgttgt ggaatgggaa   2820
attgaggccg gttccatcga agctaacaga cttaccgttc tttgatttga tgagtattgg   2880
tgggaagatt agagctggtt ttggtgcact tggcattcga ccgtcacctc caggtcgtga   2940
agaatctgtg gaggagtttg tacggcgtaa cctcggtgat gaggttttg agcgcctgat    3000 tgaaccgttt tgttcaggtg tttatgctgg tgatccttca aaactgagca tgaaagcagc   3060
gtttgggaag gtttggaaac tagagcaaaa tggtggaagc ataataggtg gtactttta   3120 ggcaattcag gagaggaaaa acgctcccaa ggcagaacga gacccgcgcc tgccaaaacc   3180
acagggccaa acagttggtt ctttcaggaa gggacttcga atgttgccag aagcaatatc   3240
tgcaagatta ggtagcaaag ttaagttgtc ttggaagctc ttaggtatca ctaagctgga   3300
gagcggagga tacaacttaa catatgagac tccagatggt ttagtttccg tgcagagcaa   3360
```

```
aagtgttgta atgacggtgc catctcatgt tgcaagcggt ctcttgcgcc ctctttctga    3420
atctgctgca aatgcactct caaaactata ttacccacca gttgcagcag tatctatctc    3480
gtacccgaaa gaagcaatcc gaacagaatg tttgatagat ggtgaactaa agggttttgg    3540
gcaattgcat ccacgcacgc aaggagttga acattagga actatctaca gctcctcact    3600 cttttccaaat cgcgcaccgc ccggaagaat tttgctgttg aacatgattg gcgggtctac    3660
aaacaccgga attctgtcca agtctgaagg tgagttagtg gaagcagttg acagagattt    3720
gaggaaaatg ctaattaagc ctaattcgac cgatccactt aaattaggag ttagggtatg    3780
gcctcaagcc attcctcagt ttctagttgg tcactttgat atccttgaca cggctaaatc    3840
atctctaacg tcttcgggct acgaagggct atttttgggt ggcaattacg tcgctggtgt    3900
agccttaggc cggtgtgtag aaggcgcata tgaaaccgcg attgaggtca acaacttcat    3960
gtcacggtac gcttacaagt aaatgtaaaa cattaaatct cccagactag ttcaaccgaa    4020
attcaattaa ggaaataaat taaggaaata caaaaagggg ggtagtcatt tgtatataac    4080
tttgtatgac ttttctcttc tattttttg tatttcctcc ctttccttt ctatttgtat    4140 tttttatca ttgcttccat tgaactgcag aaagaaggcc cggctccaag ttgttcaaga    4200
atagtggcgt tgagttttctc gacccttga cttaggatta gtcagttcta tttctcgatg    4260
gggcggggaa gggatataac tcagcggtag agtgtcacct tgacgtggtg gaagtcatca    4320
gttcgagcct gattatccct aagcccaatg tgagttttc tagttggatt tgctcccccg    4380
ccgtcgttca atgagaatgg ataagaggct cgtgggattg acgtgagggg gcagggatgg    4440
ctatatttct gggagcgaac tccgggcgaa tatgaagcgc atggatacaa gttatgcctt    4500
ggaatgaaag acaattccga atccgctttg tctacgaaca aggaagctat aagtaatgca    4560
actatgaatc tcatggagag ttcgatcctg gctcaggatg aacgctggcg gcatgcttaa    4620
cacatgcaag tcgacggga agtggtgttt ccagtggcgg acgggtgagt aacgcgtaag    4680
aacctgccct tgggagggga acaacagctg gaaacggctg ctaataccc gtaggctgag    4740 gagcaaaagg aggaatccgc ccgaggaggg gctcgcgtct gattagctag ttggtgaggc    4800
aatagcttac caaggcgatg atcagtagct ggtccgagag gatgatcagc cacactggga    4860
ctgagacacg gcccagactc ctacggggagg cagcagtggg gaattttccg caatgggcga    4920
aagcctgacg gagcaatgcc gcgtggaggt agaaggccca cgggtcgtga acttctttc    4980 ccggagaaga agcaatgacg gtatctgggg aataagcatc ggctaactct gtgccagcag    5040
ccgcggtaat acagaggatg caagcgttat ccggaatgat tgggcgcggc ggtggagctc    5100
cagcttttgt tccctttagt gagggttaat ttcgagcttg gcgtaatcat ggtcatagct    5160
gtttcctgtg tgaaattgtt atccgctcac aattccacac aacatacgag ccggaagcat    5220
aaagtgtaaa gcctggggtg cctaatgagt gagctaactc acattaattg cgttgcgctc    5280
actgcccgct ttccagtcgg gaaacctgtc gtgccagctg cattaatgaa tcggccaacg    5340
cgcggggaga ggcggtttgc gtattgggcg ctcttccgct tcctcgctca ctgactcgct    5400
gcgctcggtc gttcggctgc ggcgagcggt atcagctcac tcaaaggcgg taatacggtt    5460
atccacagaa tcaggggata acgcaggaaa gaacatgtga gcaaaaggcc agcaaaaggc    5520
caggaaccgt aaaaaggccg cgttgctggc gttttttccat aggctccgcc ccctgacga    5580 gcatcacaaa aatcgacgct caagtcagag gtggcgaaac ccgacaggac tataaagata    5640
ccaggcgttt cccctggaa gctccctcgt gcgctctcct gttccgaccc tgccgcttac    5700
```

```
cggatacctg tccgcctttc tcccttcggg aagcgtggcg ctttctcata gctcacgctg   5760
taggtatctc agttcggtgt aggtcgttcg ctccaagctg ggctgtgtgc acgaacccc    5820 cgttcagccc gaccgctgcg ccttatccgg taactatcgt cttgagtcca acccggtaag   5880
acacgactta tcgccactgg cagcagccac tggtaacagg attagcagag cgaggtatgt   5940
aggcggtgct acagagttct tgaagtggtg gcctaactac ggctacacta aggacagt    6000 atttggtatc tgcgctctgc tgaagccagt taccttcgga aaaagagttg gtagctcttg   6060
atccggcaaa caaccaccg ctggtagcgg tggttttttt gtttgcaagc agcagattac    6120
gcgcagaaaa aaggatctc aagaagatcc tttgatcttt tctacggggt ctgacgctca    6180
gtggaacgaa aactcacgtt aagggatttt ggtcatgaga ttatcaaaaa ggatcttcac   6240
ctagatcctt ttaaattaaa aatgaagttt taaatcaatc taaagtatat atgagtaaac   6300
ttggtctgac agttaccaat gcttaatcag tgaggcacct atctcagcga tctgtctatt   6360
tcgttcatcc atagttgcct gactccccgt cgtgtagata actacgatac gggagggctt   6420
accatctggc cccagtgctg caatgatacc gcgagaccca cgctcaccgg ctccagattt   6480
atcagcaata aaccagccag ccggaagggc cgagcgcaga agtggtcctg caactttatc   6540
cgcctccatc cagtctatta attgttgccg ggaagctaga gtaagtagtt cgccagttaa   6600 tagtttcgc aacgttgttg ccattgctac aggcatcgtg gtgtcacgct cgtcgtttgg    6660
tatggcttca ttcagctccg gttcccaacg atcaaggcga gttacatgat cccccatgtt   6720
gtgcaaaaaa gcggttagct ccttcggtcc tccgatcgtt gtcagaagta agttggccgc   6780
agtgttatca ctcatggtta tggcagcact gcataattct cttactgtca tgccatccgt   6840
aagatgcttt tctgtgactg gtgagtactc aaccaagtca ttctgagaat agtgtatgcg   6900
gcgaccgagt tgctcttgcc cggcgtcaat acgggataat accgcgccac atagcagaac   6960
tttaaaagtg ctcatcattg gaaaacgttc ttcgggggcg aaaactctca ggatcttacc   7020
gctgttgaga tccagttcga tgtaacccac tcgtgcaccc aactgatctt cagcatcttt   7080
tactttcacc agcgtttctg ggtgagcaaa aacaggaagg caaaatgccg caaaaaaggg   7140
aataagggcg acacggaaat gttgaatact catactcttc ctttttcaat attattgaag   7200
catttatcag ggttattgtc tcatgagcgg atacatattt gaatgtattt agaaaaataa   7260
acaaataggg gttccgcgca catttccccg aaaagtgcca cctgggaaat tgtaaacgtt   7320
aatattttgt taaaattcgc gttaaatttt tgttaaatca gctcattttt taaccaatag   7380
gccgaaatcg gcaaaatccc ttataaatca aagaataga ccgagatagg gttgagtgtt    7440
gttccagttt ggaacaagag tccactatta agaacgtgg actccaacgt caaagggcga    7500
aaaaccgtct atcagggcga tggcccacta cgtgaaccat caacctaatc aagttttttg   7560
gggtcgaggt gccgtaaagc actaaatcgg aaccctaaag ggagcccccg atttagagct   7620
tgacggggaa agccggttca atggaagcaa tgataaaaaa atacaaatag aaaaggaaag   7680
ggaggaaata caaaaaaata gaagagaaaa gtcatacaaa gttatataca aatgactacc   7740 ccccttttg tatttcctta atttatttcc ttaattgaat ttcggttgaa ctagtttgaa    7800
cgaattgtta gacattattt gccgactacc ttggtgatct cgcctttcac gtagtggaca   7860
aattcttcca actgatctgc gcgcgaggcc aagcgatctt cttcttgtcc aagataagcc   7920
tgtctagctt caagtatgac gggctgatac tgggccggca ggcgctccat tgcccagtcg   7980
gcagcgacat cctccggcgc gattttgccg gttactgcgc tgtaccaaat gcgggacaac   8040
gtaagcacta catttcgctc atcgccagcc cagtcgggcg gcgagttcca tagcgttaag   8100
```

```
gtttcattta gcgcctcaaa tagatcctgt tcaggaaccg gatcaaagag ttcctccgcc    8160
gctggaccta ccaaggcaac gctatgttct cttgcttttg tcagcaagat agccagatca    8220
atgtcgatcg tggctggctc gaagatacct gcaagaatgt cattgcgctg ccattctcca    8280
aattgcagtt cgcgcttagc tggataacgc cacggaatga tgtcgtcgtg cacaacaatg    8340
gtgacttcta cagcgcggag aatctcgctc tctccagggg aagccgaagt ttccaaaagg    8400
tcgttgatca aagctcgccg cgttgtttca tcaagcctta cggtcaccgt aaccagcaaa    8460
tcaatatcac tgtgtggctt caggccgcca tccactgcgg agccgtacaa atgtacggcc    8520
agcaacgtcg gttcgagatg gcgctcgatg acgccaacta cctctgatag ttgagtcgat    8580
acttcggcga tcaccgcttc cctcatggta aatgaaagaa agaactaaat actatatttc    8640
actttgaggt ggaaacgtaa caattttttt tattgtcttt ataatattca tattggtttt    8700
tatcgtattt attttatcca tagattataa aaattcataa agaaagacag aatgaataaa    8760
ctcaaattat tacgaatagg tcttttctaat gataaataag tatgaattcg gcgaacgtgg    8820
cgagaaagga agggaagaaa gcgaaaggag cgggcgctag ggcgctggca agtgtagcgg    8880
tcacgctgcg cgtaaccacc acacccgccg cgcttaatgc gccgctacag ggcgcgtcgc    8940
gccattcgcc attcaggctg cgcaactgtt gggaagggcg atcggtgcgg gcctcttcgc    9000
tattacgcca gctggcgaaa ggggatgtg ctgcaaggcg attaagttgg gtaacgccag    9060
ggttttccca gtcacgacgt tgtaaaacga cggccagtga attgtaatac gactcactat    9120
agggcgaatt gggtacgaaa tccttcccga tacctcccaa ggaaaatctc gaatttggat    9180
cccaaattga cgggttagtg tgagcttatc catgcggtta tgcactcttt gaataggaat    9240
ccgttttctg aaagatcctg gctttcgtac tttggtgggt ctccgagatc ctttcgatga    9300
cctatgttga agggatatct atctaatccg atcgattgcg taaagcccgc ggtagcaacg    9360
gaaccgggga agtatacag aaaagacagt tcttttctat tatattagta ttttctatta    9420
tattagatat attagactat tatattagat tagtattagt tagtgatccc gacttagtga    9480
gtctgatgaa ttgttggcac cagtcctaca ttttgtctct gtggaccgag gagaaaaggg    9540
gctcggcggg aagaggagtg taccatgaga gaagcaagga ggtcaacctc tttcaaatat    9600
acaacatgga ttctggcaat gtagttggac tctcatgtcg atccgaatga atcatccttt    9660
ccacggaggt aaatctttgc ctgctaggca agaggatagc aagttccaaa ttctgtctcg    9720
gtaggacatg tatttctatt actatgaaat tcataaatga agtagttaat ggtagggtta    9780
ccattatcct ttttgtagtg acgaatcttg tatgtgttcc taagaaaagg aatttgtcca    9840
tttttcgggg tctcaaaggg gcgtggaaac gcataagaac tcttgaatgg aaaagagatg    9900
taactccagt tccttcggaa tcggtagtca atcctatttc cgatagggga agttgacaat    9960
tgaatccgat tttgaccatt attttcatat ccgtaatagt gcgactgcag a           10011
```

<210> SEQ ID NO 5
<211> LENGTH: 28
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(28)

<400> SEQUENCE: 5
gttctagaga cattacgttc tccccttg                                       28

```
<210> SEQ ID NO 6
<211> LENGTH: 29
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(29)

<400> SEQUENCE: 6
agatatccat ggtgaatctc ctgttgatt                                    29

<210> SEQ ID NO 7
<211> LENGTH: 34
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(34)

<400> SEQUENCE: 7
gccagaattc accacgatcg aacgggaatg gata                              34

<210> SEQ ID NO 8
<211> LENGTH: 29
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(29)

<400> SEQUENCE: 8
gctctagaga ttcggaattg tctttcctt                                    29

<210> SEQ ID NO 9
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(37)

<400> SEQUENCE: 9
gaagatgcca tggattaaat ctcctaagtt attaaag                           37

<210> SEQ ID NO 10
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(37)

<400> SEQUENCE: 10
cgaatctctt cccgggtaga gggagacctc atctttg                           37

<210> SEQ ID NO 11
<211> LENGTH: 38
```

<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(38)

<400> SEQUENCE: 11
ctccctctac ccgggaagag attcggaatt gtctttcc                    38

<210> SEQ ID NO 12
<211> LENGTH: 38
<212> TYPE: DNA
<213> ORGANISM: artificial sequence
<220> FEATURE:
<223> OTHER INFORMATION: PRIMER
<220> FEATURE:
<221> NAME/KEY: misc_feature
<222> LOCATION: (1)..(38)

<400> SEQUENCE: 12
cgcttagtca tgataaaatc ttggtttatt taatcatc                    38

<210> SEQ ID NO 13
<211> LENGTH: 85
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(85)

<400> SEQUENCE: 13
aattcgttaa agaatgtagc tgactgcata cttaaaccac ccatactagt tgctgggtgg    60
tttttatgtt ataatataaa tgtgt                                         85

<210> SEQ ID NO 14
<211> LENGTH: 85
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(85)

<400> SEQUENCE: 14
ctagacacat ttatattata acataaaaac cacccagcaa ctagtatggg tggtttaagt    60
atgcagtcag ctacattctt taacg                                         85

<210> SEQ ID NO 15
<211> LENGTH: 194
<212> TYPE: DNA
<213> ORGANISM: artificial sequence
<220> FEATURE:
<223> OTHER INFORMATION: chimeric X2/kvp1
<220> FEATURE:
<221> NAME/KEY: misc_feature
<222> LOCATION: (1)..(194)

<400> SEQUENCE: 15
aattcgttaa agaatgtagc tgactgcata cttaaaccac ccatactagt tgctgggtgg    60
tttttatgtt ataatataaa tgtgtctaga gacattacgt tctcccttg agtgatacac   120

-continued

```
aatgagaacc aactcgtttc aagtagtacc tcacataact tatcttttaa atcaacagaa      180
ggagattcac catg                                                        194
```